(12) United States Patent
Leibl et al.

(10) Patent No.: US 9,181,204 B2
(45) Date of Patent: Nov. 10, 2015

(54) CHEMICAL COMPOUNDS CAPABLE OF COMPLEXING AT LEAST ONE METAL ELEMENT AND A COORDINATION COMPLEX BASED ON THESE COMPOUNDS

(75) Inventors: Winfried Leibl, Coulombs (FR); Boris Vauzeilles, Sceaux (FR); Aurelie Baron, L'isle Adam (FR); Ally Aukauloo, Massy (FR); Christian Herrero, Paris (FR); Marie-France Charlot, Orsay (FR)

(73) Assignees: Commissariat a l'energie atomique et aux energies alternatives, Paris (FR); CENTRE NATIONAL DE LA RECHERCHE SCIENTIFIQUE, Paris (FR); UNIVERSITE PARIS SUD XI, Orsay (FR)

( * ) Notice: Subject to any disclaimer, the term of this patent is extended or adjusted under 35 U.S.C. 154(b) by 577 days.

(21) Appl. No.: 13/514,227

(22) PCT Filed: Dec. 7, 2010

(86) PCT No.: PCT/EP2010/069091
§ 371 (c)(1),
(2), (4) Date: Jul. 23, 2012

(87) PCT Pub. No.: WO2011/070025
PCT Pub. Date: Jun. 16, 2011

(65) Prior Publication Data
US 2012/0283442 A1 Nov. 8, 2012

(30) Foreign Application Priority Data
Dec. 8, 2009 (FR) ..................................... 09 58753

(51) Int. Cl.
*C07D 249/04* (2006.01)
*C07D 401/14* (2006.01)
*C07D 249/06* (2006.01)
*C07F 19/00* (2006.01)

(52) U.S. Cl.
CPC ............ *C07D 249/06* (2013.01); *C07D 401/14* (2013.01); *C07F 19/005* (2013.01)

(58) Field of Classification Search
None
See application file for complete search history.

(56) References Cited

FOREIGN PATENT DOCUMENTS

| WO | 2006002009 | * 11/2006 | ......... A61K 31/4184 |
| WO | 2009106885 | * 9/2009 | ........... C07D 413/14 |

OTHER PUBLICATIONS

Paek. Journal of Organometallic Chemistry, 2010, 85, 821-26.*
Constable. Inorganic Chemistry Communications, 2010, 13, 495-97.*
Fletcher. Organometallics, 2008, 27, 5430-33.*
International Search Report issued Jan. 20, 2011, in PCT/EP2010/069091.
French Preliminary Search Report issued Jul. 2, 2010, in Patent Application No. FR 0958753.
Andreas Winter, et al., "Azido- and Ethynyl-Substituted 2,2':6',2"-Terpyridines as Suitable Substrates for Click Reactions", Synthesis, No. 9, XP 002580328, 2009, pp. 1506-1512.
Toma N. Glasnov, et al., "Microwave-Assisted Click Chemistry for the Preparation of 3- and 4-Triazolyl-2(1H)-quinolones as Potential Fluorescent Probes", QSAR & Combinatorial Science, vol. 26, No. 11-12, XP 002580329, 2007, pp. 1261-1265.
Fabien Lachaud, et al., "A Biomimetic Model of the Electron Transfer between $P_{680}$ and the TyrZ-His190 Pair of PSII", Angew. Chem. Int. Ed., vol. 44, XP 008090906, 2005, pp. 1536-1540.
Petra J. Cameron, et al., "Electrochemical studies of the Co(III)/Co(II)(dbbip)$_2$ redox couple as a mediator for dye-sensitized nanocrystalline solar cells", Coordination Chemistry Reviews, vol. 248, 2004, pp. 1447-1453.
Martin Sjodin, et al., "Proton-Coupled Electron Transfer from Tyrosine in a Tyrosine-Ruthenium-tris-Bipyridine Complex: Comparison with Tyrosine: Oxidation in Photosystem II", J. Am. Chem. Soc., vol. 122, No. 16, 2000, pp. 3932-3936.

* cited by examiner

*Primary Examiner* — Noble Jarrell
(74) *Attorney, Agent, or Firm* — Oblon, McClelland, Maier & Neustadt, L.L.P.

(57) ABSTRACT

The present invention relates to compounds of formula (I):

A-T-Z    (I)

in which: the group A is a bipyridine group capable of complexing at least one metal element; the group T is a triazole group directly bound to the group A; and the group Z is a halogen atom, a nitro group, a cyano group, an alkyl group, an aryl group, a heterocyclic group, a group of formula —$NR^1R^2$, a group of formula —$SR^1$, a group of formula —$S(=O)_2(OR^1)$, a group of formula —O—$S(=O)_2(OR^1)$, a group of formula —O—$S(=O)_2(R^1)$, a group of formula —$S(=O)(OR^1)$, a group of formula —$S(=O)(R^1)$, a group of formula —$S(=O)_2R^1$, a group of formula —$PR^1R^2$, a group of formula —$P(=O)(OR^1)(OR^2)$, a group of formula —O—$P(=O)(OR^1)(OR^2)$, a group of formula —O—$P(=O)(OR^1)(R^2)$, a group of formula —$OR^1$ or a group of formula —CO—$R^1$.

15 Claims, No Drawings

CHEMICAL COMPOUNDS CAPABLE OF COMPLEXING AT LEAST ONE METAL ELEMENT AND A COORDINATION COMPLEX BASED ON THESE COMPOUNDS

TECHNICAL FIELD

This application is a National Stage application of International Application No. PCT/EP2010/069091 filed Dec. 7, 2010, the entire contents of which is hereby incorporated herein by reference. This application also claims priority under 35 U.S.C. §119 to FR Patent Application No. 0958753, filed Dec. 8, 2009, the entire contents of which is hereby incorporated herein by reference.

The present invention relates to novel chemical compounds capable of complexing at least one metal element as well as to coordination complexes of these compounds with one or several metal elements such as ruthenium.

These compounds and the coordination complexes based on the latter potentially have photochemical properties, i.e. they may induce conversion of light energy into chemical energy by producing notably electrons and/or protons which may then be involved in chemical reactions, such as oxidation-reduction chemical reactions.

Consequently, these compounds may find their application in many fields involving light as a source of energy, such as the field for producing fuels, the field for producing synthetic products involving oxidation-reduction reactions, the field of therapy or diagnostics also involving oxidation-reduction reactions, the field of production of electricity.

STATE OF THE PRIOR ART

Because of their very diverse fields of applications, many research teams thus set their goal of developing compounds capable of having photochemical properties, after binding of a metal element by complexation.

This is notably the case of Graetzel et al., (in Coord. Chem. Rev., 2004, 248, 1447-1453), which sets up a complex based on ruthenium of formula [Ru(Bipy(COO)$_2$)$_2$(NCS)$_2$], the ruthenium thus being chelated by two bipyridine groups bearing two carboxyl groups (symbolized in the formula by (Bipy (COO)$_2$)$_2$ and two isothiocyanato groups (symbolized in the formula by (NSC)$_2$). This complex is used in photovoltaic devices, where it is adsorbed at the surface of an electrode comprising titanium dioxide grains, this electrode playing the role of an anode. In contact with visible light, this complex absorbs photons and in return ejects electrons, which are captured by the conduction band of the titanium dioxide making up the grains of the electrode, said electrons are then conveyed towards a cathode connected to the anode, where they induce the reduction of a redox pair playing the role of an electronic relay (I$_3^-$/I$^-$).

In order to widen the panel of applications of the compounds capable of complexing metal elements and which may thus have photochemical properties, some authors worked on the design of organic compounds comprising, in addition to the complexing groups, other groups bound to said complexing groups, notably by means of spacer groups, these other groups may have different functionalities, such as anchoring by a covalent bond on various supports, catalytic properties and/or addressing properties (i.e. a capability of having affinity for a target, such as a given cell, a cell compartment). These compounds may be described as modular compounds.

Thus, some authors developed such modular compounds by associating the aforementioned groups by means of spacer groups, such as amidic spacer groups (as described in J. Am. Chem. Soc., 2000, 122, 3932-3936) or imidazole spacer groups (as described in Angew. Chem. Int. Ed., 2005, 44, 1536-1540). However, the production of such compounds by using this type of spacer groups is accomplished under conditions which are difficult to apply, notably on a large scale.

In order to overcome these synthesis drawbacks, some authors set into place modular compounds by coupling a complexing group with another group on the basis of a coupling reaction between said groups, simple and efficient to apply: the reaction for 1,3-dipolar cyclo-addition of the Huisgen type of a group bearing an azide function and of a group bearing an alkyn function, by means of which a compound is obtained comprising a complexing group bound to another group by means of a triazole spacer group. This is notably the case of Winter et al. in Synthesis, 2009, No. 9, p. 1506-1512, which describes compounds comprising a terpyridine group bound to other groups (notably aryl groups) by means of a triazole spacer group, the terypridine group complexing the ruthenium. The authors of this publication ascertained that there was poor electron communication between the aryl group and the terpyridine group separated from each other by a triazole group and ascribed this poor electron conduction to the poor conductive properties of this triazole group.

Therefore, with view to the prior art, it exists a real a priori technique, to use a triazole group forming a bridge between two groups, for which at least one of the groups is a group complexing at least one metal element, in order to obtain compounds:

having photochemical properties; and
having good electron conduction between the complexing group and the other group via a triazole spacer group.

The authors of the present invention set themselves the goal of proposing novel compounds for which at least one of the constitutive groups of said compound is a complexing group of at least one metal element, having after complexation with a metal element, photochemical properties in the presence of a light stimulus, which complexing group being bound to another group which may have diverse functionalities (for example an anchoring functionality on a support, a catalytic functionality, etc.) via a spacer group, the electron conduction has to be effective between the complexing group and said other group.

DISCUSSION OF THE INVENTION

The present authors surprisingly discovered and in spite of the a priori existing technique, that by selecting a complexing group suitably, it is possible to obtain compounds comprising said complexing group bound bound to another group via a triazole spacer group, without interrupting or lowering the electron conduction between the complexing group and the other group, by the triazole spacer group, as this is the case with the compounds of the prior art.

Thus, the invention relates to a compound fitting the following formula (I):

A-T-Z     (I)

wherein:

*A is a group capable of being complexing at least one metal element, selected from pyridine, bipyridine, phenanthroline or phthalocyanine groups;

*T is a triazole group directly bound to group A;

*Z is a halogen atom, a nitro group, a cyano group, an alkyl group, an aryl group, a heterocyclic group, a group of formula —NR$^1$R$^2$, a group of formula —SR$^1$, a group of formula —S(=O)$_2$(OR$^1$), a group of formula —O—S(=O)$_2$(OR$^1$), a group of formula —O—S(=O)$_2$(R$^1$), a group of formula —S(=O)(OR$^1$), a group of formula —S(=O)(R$^1$), a group of formula —S(=O)₂R¹, a group of formula —PR¹R², a group of formula —P(=O)(OR¹)(OR²), a group of formula —O—P(=O)(OR¹)(OR²), a group of formula —O—P(=O)(OR¹)(R²), a group of formula —OR¹ or a group of formula —CO—R¹, and R², independently represent a hydrogen atom, an alkyl group or an aryl group, said alkyl or aryl groups being optionally substituted.

By suitably selecting the group A, the authors surprisingly discovered that this group allowed improvement in the electron conductivity of the triazole group to which it is bound, while this triazole group is known to be a poor electron conductor, notably when it is bound to groups, such as a terpyridine group. The compounds may thus be used as compounds capable of conducting electron charges and of conveying them for example towards a device on which they may be grafted (by suitably selecting a group Z having functions capable of being grafted to the surface of such a device).

Furthermore, the triazole group is very stable thermally and chemically and notably withstands very hard oxidation and reduction conditions.

Group A as mentioned above also has a capability of complexing metal elements, such as ruthenium.

The compounds of the invention are also of a simple design, because of the possibility of connecting the group A to the group Z by a simple coupling reaction, a so-called <<click-chemistry reaction>> between an azide function and an alkyn function in order to obtain the triazole T group.

According to the invention, group A of the compounds of the invention is a pyridine, bipyridine, phthalocyanine or phenanthroline group, said groups may optionally be substituted.

By a pyridine group, is meant a group of the following formula:

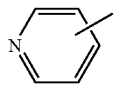

the bond located in the middle of the carbon-carbon bond indicating that the binding to the triazole group may be accomplished by any of the carbon atoms forming the pyridine ring. The aforementioned pyridine group may be substituted with one or several substituents located at the constitutive carbon atoms of the pyridine ring except for the one which is bound to the group T.

By group bipyridine, is meant a group of the following formula:

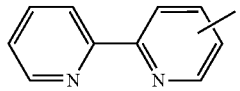

the bond located in the middle of the carbon-carbon bond indicating that the binding to the triazole group may be accomplished by any of the constitutive carbon atoms of the bipyridine ring. The aforementioned bipyridine group may be substituted with one or several substituents located at the constitutive carbon atoms of the ring except for the one which is bound to the group T.

By phthalocyanine group, is conventionally meant a group of the following formula:

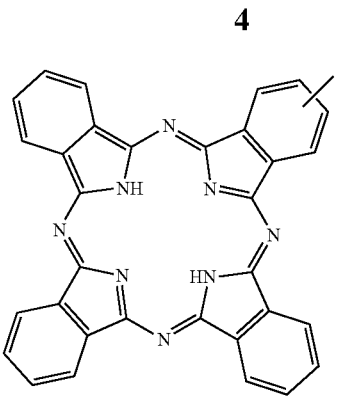

the bond located in the middle of the carbon-carbon bond indicating that the binding to the triazole group may be accomplished by any of the constitutive carbon atoms of the phenyl rings of the phthalocyanine group. The aforementioned phthalocyanine group may be substituted with one or several substituents located at the constitutive carbon atoms of the phenyl rings except for one which is bound to the group T.

By phenanthroline group, is conventionally meant a group of the following formula:

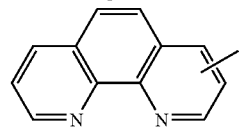

the bond located in the middle of the carbon-carbon bond indicating that the binding to the triazole group may be accomplished through any of the constitutive carbon atoms of the phenanthroline cycle. The aforementioned phenanthroline group may be substituted with one or several substituents located at the constitutive carbon atoms of the ring except for the one which is bound to the group T.

When group A is substituted, it may be substituted with at least one halogen atom and/or at least one group selected from alkyl, aryl, amino, alkoxy or hydroxyl groups.

Advantageously, group A is a bipyridine group fitting the following formula:

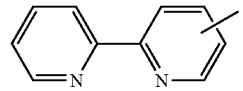

the bond intersecting one of the rings indicating that the bipyridine group may be bound to any of the constitutive carbon atoms of the bipyridine rings to the triazole group T.

As mentioned above, group T is a triazole group directly bound to the aforementioned group A (i.e. it is directly bound to one of the constitutive carbon atoms of the aromatic ring(s) of the group A), the triazole group fitting the following formula:

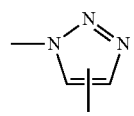

the bond cutting the carbon-carbon double bond indicating that the triazole group is bound to group A or group Z via one of the constitutive carbon atoms of this double bond while the bond attached to the nitrogen atom indicates that the triazole is bound to the other group (A or Z) by means of this nitrogen atom.

As mentioned above, Z may be a halogen atom, a nitro group, a cyano group, an alkyl group, an aryl group, a heterocyclic group, a group of formula —NR$^1$R$^2$, a group of formula —SR$^1$, a group of formula —S(=O)$_2$(OR$^1$), a group of formula —O—S(=O)$_2$(OR$^1$), a group of formula —O—S(=O)$_2$(R$^1$), a group of formula —S(=O)(OR$^1$), a group of formula —S(=O)(R$^1$), a group of formula —S(=O)$_2$R$^1$, a group of formula —PR$^1$R$^2$, a group of formula —P(=O)(OR$^1$)(OR$^2$), a group of formula —O—P(=O)(OR$^1$)(OR$^2$), a group of formula —O—P(=O)(OR$^1$)(R$^2$), a group of formula —OR$^1$ or a group of formula —CO—R$^1$, R$^1$ and R$^2$ representing independently of each other a hydrogen atom, an alkyl group or an aryl group, said alkyl or aryl groups being optionally substituted (whether this be for the group Z when it represents an alkyl or an aryl group or for the groups R$^1$ and R$^2$ when they represent an alkyl or aryl group).

By a halogen atom, is conventionally meant in the foregoing and in the following, an atom which may be a chlorine atom, a bromine atom, a fluorine atom, an iodine atom.

By a nitro group, is conventionally meant in the foregoing and in the following, a group of formula —NO$_2$.

By a cyano group, is conventionally meant in the foregoing and in the following, a group of formula —CN.

By optionally substituted alkyl group, it is specified that this may be a linear or branched alkyl group, for example comprising from 1 to 6 carbon atoms, such as a methyl, ethyl, n-propyl, i-propyl, n-butyl, i-butyl, t-butyl group, at least one of the hydrogen atoms of the alkyl group may be substituted, for example with a halogen atom, a nitro group, a cyano group, an alkyl group, an aryl group, a heterocyclic group, a group of formula —NR$^1$R$^2$, a group of formula —SR$^1$, a group of formula —S(=O)$_2$(OR$^1$), a group of formula —O—S(=O)$_2$(OR$^1$) a group of formula —O—S(=O)$_2$(R$^1$), a group of formula —S(=O)(OR$^1$), a group of formula —S(=O)(R$^1$), a group of formula —S(=O)$_2$R$^1$, a group of formula —PR$^1$R$^2$, a group of formula —P(=O)(OR$^1$)(OR$^2$), a group of formula —O—P(=O)(OR$^1$)(OR$^2$), a group of formula —O—P(=O)(OR$^1$)(R$^2$), a group of formula —OR$^1$ or a group of formula —CO—R$^1$, a group of formula —CO$_2$R$^1$, R$^1$ and R$^2$ independently representing a hydrogen atom, an alkyl group or an aryl group, said alkyl or aryl groups being optionally substituted.

By optionally substituted aryl group, it is specified that this may be an aryl group comprising from 6 to 18 carbon atoms, such as a phenyl group, a naphthyl group, at least one of the hydrogen atoms borne by at least one of the aromatic rings of the group being optionally substituted, for example, with a halogen atom, a nitro group, a cyano group, an alkyl group, an aryl group, a heterocyclic group, a group of formula —NR$^1$R$^2$, a group of formula —SR$^1$, a group of formula —S(=O)$_2$(OR$^1$), a group of formula —O—S(=O)$_2$(OR$^1$), a group of formula —O—S(=O)$_2$(R$^1$), a group of formula —S(=O)(OR$^1$), a group of formula —S(=O)(R$^1$), a group of formula —S(=O)$_2$R$^1$, a group of formula —PR$^1$R$^2$, a group of formula —P(=O)(OR$^1$)(OR$^2$), a group of formula —O—P(=O)(OR$^1$)(OR$^2$), a group of formula —O—P(=O)(OR$^1$)(R$^2$), a group of formula —OR$^1$ or a group of formula —CO—R$^1$, a group of formula —CO$_2$R$^1$, R$^1$ and R$^2$ independently representing a hydrogen atom, an alkyl group or an aryl group, said alkyl or aryl groups being optionally substituted.

Advantageously, Z may be an aryl group, optionally substituted with at least one halogen atom and/or at least one —NR$^1$R$^2$ or —CO$_2$R$^1$ group, R$^1$ and R$^2$ being as defined above.

Because of its chemical nature, the group Z may fulfill different functions:

Z may be intended for allowing grafting of the compounds of the invention on a support, this grafting intervening by a chemical reaction between a function borne by the group Z and a function of the support, the support may for example be a silica support, a titanium oxide support, a silicon support, a metal support (such as a gold support), a carbon support, a tin and indium oxide support (also entitled an ITO <<Indium Tin Oxide>> support), which support may be an electrode of a photovoltaic device;

Z may be intended for fulfilling a catalytic function, i.e. that the group Z may bring electrons from the group A after complexation of the latter to a metal element, followed by light excitation, towards other compounds in order to ensure an oxidation-reduction reaction of these compounds;

Z may be intended for fulfilling a function for controlling the properties of another group to which it is bound, for example of the group A;

Z may be intended for fulfilling an addressing function, i.e. it may have chemical affinity for a given target, such as a given cell, a given cell compartment, a given molecule (such as a nucleic acid molecule).

Particularly advantageous compounds according to the invention are compounds for which A is a bipyridine group and Z is an optionally substituted aryl group.

Compounds meeting this definition are compounds fitting the following formula (II):

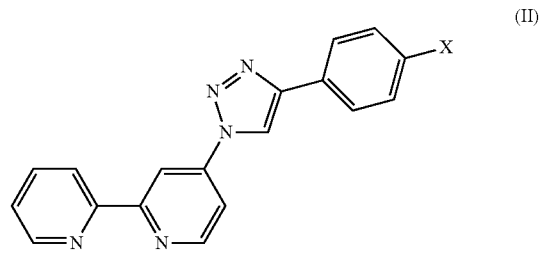

(II)

X representing a hydrogen atom, a halogen atom, an —NR$^1$R$^2$ group or an —CO$_2$R$^1$, R$^1$ and R$^2$ fitting the same definition as the one given above.

Most particularly, X may be a hydrogen atom, a fluorine atom, a —N(CH$_3$)$_2$ group or a —CO$_2$—CH$_3$ group.

As mentioned above, the compounds of the invention are easy to design, insofar that they may be synthesized by a simple coupling reaction between an azide (or alkyn) function borne by a group A or a precursor of the latter and an alkyn (or azide) function borne by a group Z or precursor of the latter according to the principle of 1,3-dipolar cycloaddition of the Huisgen type, by means of which the triazole group T is obtained, forming a bridge between the group A and the group Z. This coupling reaction may be catalyzed by copper in the form of a salt (such as copper sulfate in the presence of a reducing agent such as sodium ascorbate, or further such as copper iodide CuI or copper bromide CuBr). This reaction may be applied in a solvent comprising water.

As mentioned above, the compounds of the invention comprise a specific group A capable of complexing at least one metal element, i.e. binding at least one metal element through at least one coordination bond.

Thus, the invention relates according to a second object to coordination complexes of at least one metal element with at least one compound of the invention as defined above.

It is specified that, by a coordination complex, is conventionally meant a polyatomic structure comprising the metal element around which groups belonging to the compounds of the invention (in this instance, in our case, the group A) are bound by coordination bonds, the coordination bond being generated by bringing an electron doublet belonging to said groups into an empty orbital of the metal element.

The metal element may be a transition metal, such as Ti, Zr, Hf, V, Nb, Re, Ru, Ta, a lanthanide element, an actinide element as well as the elements Al, Ga, Ge, In, Sn, Sb, Tl, Pb, Bi and Po.

In particular, the metal element is advantageously a transition metal, such as ruthenium Ru.

In addition to the compounds according to the invention, the complexes defined above may comprise compounds other than those of the invention capable of complexing said metal element, such as ligand compounds such as pyridine and bipyridine.

Particularly advantageous compounds of the invention capable of entering the structure of complexes of the invention are compounds of the following formula (II):

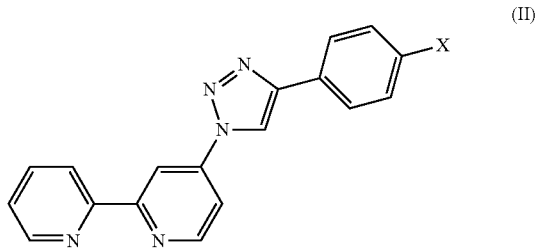

X representing a hydrogen atom, a halogen atom, a —NR$^1$R$^2$ group or a —CO$_2$R$^1$ group, R$^1$ and R$^2$ fitting the same definition as the one given above, these compounds may be used in combination with the same complex with other compounds such as bipyrine.

Thus, advantageous complexes according to the present invention may fit the following formula (III):

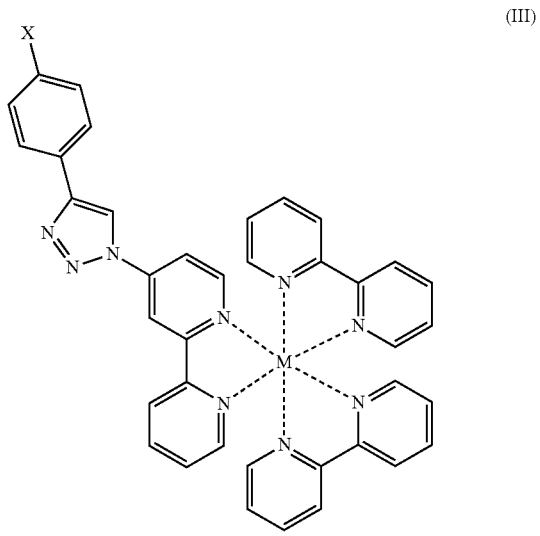

with X being as defined above and M being a metal element such as ruthenium, the bonds in dotted lines representing coordination bonds.

In particular, X may be a hydrogen atom, a fluorine atom, a diethylamino group —N(CH$_3$)$_2$ or a —CO$_2$CH$_3$ group.

With such complexes, the metal element under the action of photons may thereby be found in an excited state thereby releasing one electron which may circulate via the triazole group, a good electron conductor by the specific selection of the group A, and via the group Z, the transfer being notably accomplished rapidly when the group Z includes an electron acceptor function (such as a halogen atom like fluorine).

When the group Z includes an electron donor function (notably when Z is a phenyl group substituted with at least one —NR$^1$R$^2$ group), a rapid electron transfer may occur under the action of photons from group Z towards group A complexed with a metal element.

It may thus be inferred therefrom that the triazole group forming a bridge between the group A and the group Z allows preferential photo-induced electron transfer within the ligand from the most donor group towards the most acceptor group, a property which is much sought in fields where photo-induced electron transfer phenomena occur.

It should also be noted that, if the triazole group allows rapid transfer of electrons between the group A or Z or vice versa, it does not however change by any means the excited states of the metal element complexed by the group A.

The compounds of the invention and the coordination complexes derived from them, because of the capability of rapidly transferring electrons from the group A to the group Z and vice versa, which itself may enter into contact with another entity which will accept said electron (for example, an electrode, a chemical compound, a biological cell) will find application in all the fields where electron transfer is required, which is the case in the following fields:

the field of fuel production involving oxidation-reduction reactions, such as the production of hydrogen and of oxygen by photo-induced breakdown of water or photo-induced reduction of carbon dioxide, these reactions being ecologically compatible means for producing fuels from a renewable energy source, light energy; in this case, the complexes of the invention may be included in a photo-catalysis cell, more particularly in a photo-anode, for example in titanium dioxide, where oxidation of the reagent occurs (for example, water being oxidized into oxygen), the electrons produced by this reaction being then lead towards a photo-cathode where the reduction of another reagent occurs (for example, reduction of protons), the products stemming from the oxidation and reduction reactions may be used as a fuel;

the field for producing synthetic products, which are made by oxidation or reduction of a precursor;

the field of therapy or diagnostics, in which it may be necessary to oxidize or reduce a biological molecule;

the field of production of electricity, the complexes of the invention may thus enter the structure of photovoltaic devices.

It is understood that applications other than the aforementioned ones may be contemplated, from the moment that they involve a photo-induced transfer of electrons.

The invention will now be described on the basis of the following examples given as an illustration and not as a limitation.

DETAILED DISCUSSION OF PARTICULAR EMBODIMENTS

EXAMPLE 1

This example illustrates the preparation of a precursor compound required for preparing the compounds of the invention: 4'-azido-2,2'-bipyridine N'-oxide, this intermediate compound fitting the following formula:

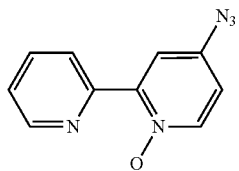

This precursor compound is prepared by nitration of 2,2'-bipyridine N'-oxide in order to obtain 4'-nitro-2,2'-bipyridine N'-oxide followed by displacement of the nitro group by a nitride group, these reactions may be summarized by the following reaction scheme:

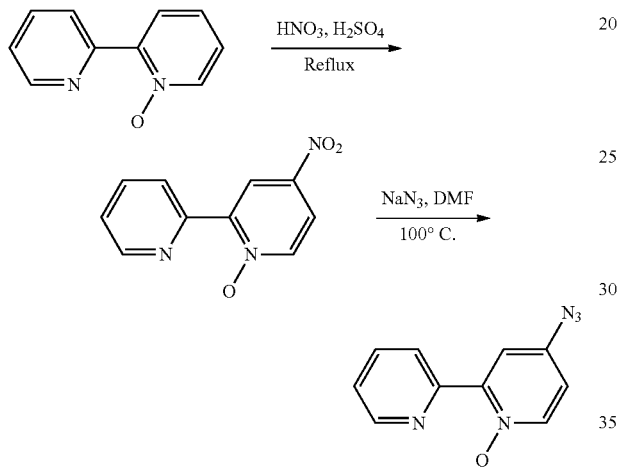

The operating procedure for preparing 4'-nitro-2,2'-bipyridine N'-oxide is the following:

2,2'-bipyridine N'-oxide (2.00 g, 11.6 mmol) is dissolved in concentrated sulfuric acid (12.0 mL, 22.1 g, 225 mmol, 19.4 equiv.) with stirring. Fuming nitric acid (19.0 mL, 28.9 g, 459 mmol, 39.5 equiv.) in concentrated sulfuric acid (10.0 mL, 18.4 g, 188 mmol, 16.2 equiv.) is added for 10 minutes in the previous mixture and the thereby obtained reaction mixture is refluxed (i.e. at 120° C.) for 4.5 hours. The reaction mixture is then poured into ice (80 g) and neutralized, with cooling by the ice bath, by adding an aqueous 38% soda solution until a pH of 8 is obtained. The formed precipitate with a slightly yellow color is filtered and washed with water. The solid precipitate is then dissolved in methylene chloride, water is added and the resulting mixture is extracted with methylene chloride. The organic phases are then combined, dried with sodium sulfate, filtered and then concentrated in order to obtain 834 mg (33% yield) of a beige solid consisting in 4'-nitro-2,2'-bipyridine N'-oxide of the following formula:

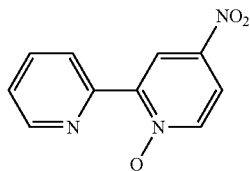

The operating procedure for preparing 4'-azido-2,2'-bipyridine N'-oxide is the following:

4'-nitro-2,2'-bipyridine N'-oxide (400 mg, 1.84 mmol, 1 equiv.) and sodium nitride (426 mg, 6.55 mmol, 3.6 equiv.) were suspended in anhydrous dimethylformamide (DMF) (20.0 mL) and then heated to 100° C. for 20 hours under an argon atmosphere. After evaporation, water is added (25 mL) and the mixture is extracted with methylene chloride (3*20 mL). Combined organic phases are dried with sodium sulfate, filtered and concentrated in order to obtain a brownish oil. The obtained crude material is purified by chromatography on a column with silica gel ($CH_2Cl_2/CH_3OH$, 95/5) in order to obtain 190 mg (i.e. 49% yield) of 4'-azido-2,2'-bipyridine N'-oxide of the following formula:

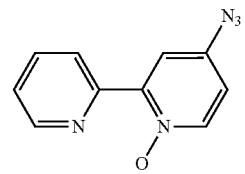

EXAMPLE 2

This example illustrates the preparation of a compound according to the invention:

4'-(4"-phenyl-1H-1",2",3"-triazol-1"-yl)-2,2'-bipyridine fitting the following formula:

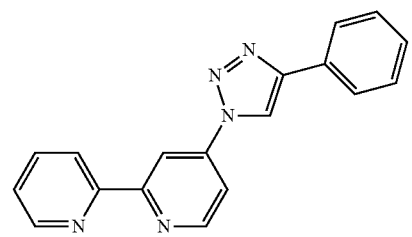 [SMILES: c1ccc(-c2cn(-c3ccnc(-c4ccccn4)c3)nn2)cc1]

This compound is prepared in two steps: a first step for preparing 4'-4"-phenyl-1H-1",2",3"-triazol-1"-yl)-2,2'-bipyridine N-oxide and a second step for preparing 4'-4"-phenyl-1H-1",2",3"-triazol-1"-yl)-2,2'-bipyridine, these steps may be summarized by the following reaction scheme:

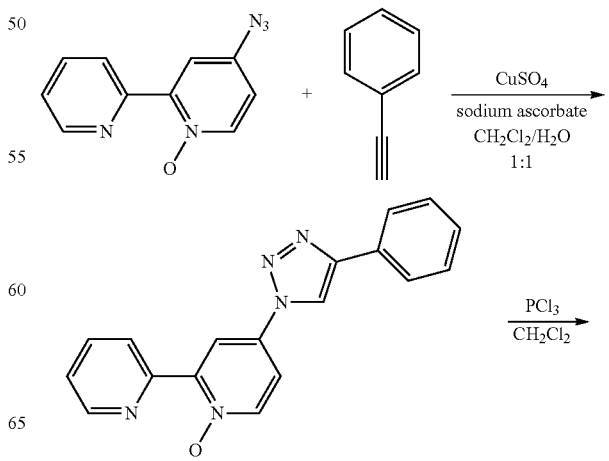

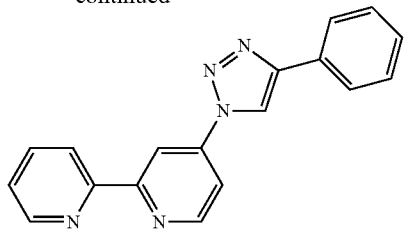

a) Preparation of 4'-(4"-phenyl-1H-1",2",3"-triazol-1"-yl)-2,2'-bipyridine N'-oxide 4'-azido-2,2'-bipyridine-N'-oxide prepared according to Example 1 (42.6 mg, 200 µmol, 1 equiv.) is suspended in methylene chloride (1.67 mL) under an argon atmosphere. Phenyl acetylene (22.0 µL, 20.4 mg, 200 µmol, 1 equiv.) is added to the previous mixture and then water (1.51 mL), sodium ascorbate (80 µL, 49.5 mg per mL of water, 20 µmol, 0.1 equiv.) and copper sulfate pentahydrate (80 µL, 31.2 mg per mL of water, 10 µmol, 0.05 equiv.) are added sequentially. The reaction mixture is stirred at room temperature for 20 hours. After this period, thin layer chromatography in CH$_2$Cl$_2$/methanol (9/1) shows that the coupling reaction is quantitative. The reaction mixture is then diluted with 6 mL of a CH$_2$Cl$_2$/H$_2$O (1/1) mixture and is extracted with methylene chloride (3*6 mL). The organic phases are combined and washed with water, dried with sodium sulfate, filtered and concentrated in order to obtain 61.5 mg (i.e. 98% yield) of a slightly yellow solid consisting in 4'-(4"-phenyl-1H-1",2",3"-triazol-1"-yl)-2,2'-bipyridine N'-oxide of the following formula:

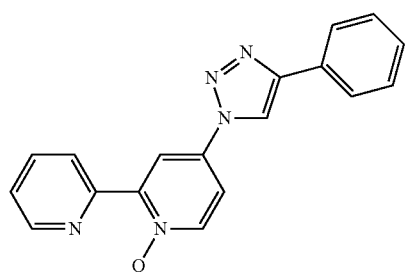

b) Preparation of 4'-(4"-phenyl-1H-1",2",3"-triazol-1"-yl)-2,2'-bipyridine

To a solution of 4'-(4"-phenyl-1H-1",2",3"-triazol-1"-yl)-2,2'-bipyridine N'-oxide prepared beforehand (59.8 mg, 190 µmol, 1 equiv.) in methylene chloride (3.8 mL) under an argon atmosphere, is added phosphorus trichloride (49.7 µL, 78.3 mg, 570 µmol, 3.0 equiv.) at 0° C. The reaction mixture is refluxed for 3 hours, and then poured into 4 mL of ice and neutralized with an aqueous 38.5% sodium hydroxide solution. The aqueous phase is extracted several times with methylene chloride (3*5 mL). The organic phases are then combined and washed with water, and then dried with sodium sulfate, filtered and concentrated. The residue is purified by flash chromatography on silica gel (CH$_2$Cl$_2$/methanol, 95/5), in order to obtain 49.2 mg (i.e. 87% yield) of a slightly yellow solid corresponding to 4'-(4"-phenyl-1H-1",2",3"-triazol-1"-yl)-2,2'-bipyridine of the following formula:

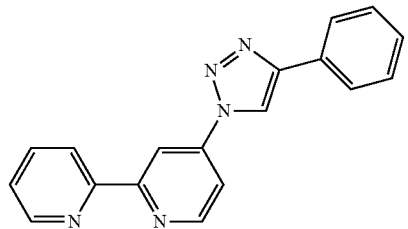 [SMILES: c1ccc(-c2cn(-c3ccnc(-c4ccccn4)c3)nn2)cc1]

A coordination complex of the following formula:

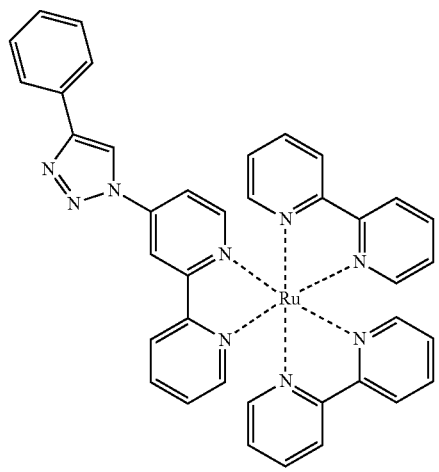

was prepared from the compound synthesized above and from bipyridine compounds.

It was proceeded with measurements of the absorption and emission spectra of this complex, which have a maximum absorption peak at 458 nm and a maximum emission peak at 632 nm (as compared with 451 nm and 608 nm respectively for a ruthenium complex comprising three bypyridine non-substituted groups). It may thus be inferred therefrom that the presence of a triazole group does not perturb the absorption and emission characteristics of the chromophore based on ruthenium.

EXAMPLE 3

This example illustrates the preparation of a compound according to the invention: 4'-(4"-(4'''-(dimethylamino)phenyl)-1H-1",2",3"-triazol-1"-yl)-2,2'-bipyridine fitting the following formula:

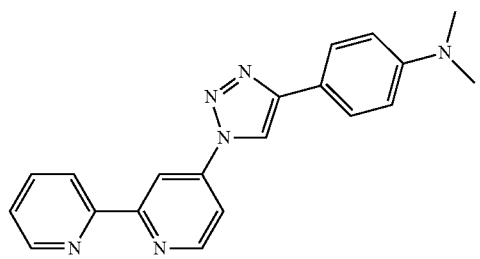 [SMILES: CN(C)c1ccc(-c2cn(-c3ccnc(-c4ccccn4)c3)nn2)cc1]

This compound is prepared in two steps: a first step for preparing 4'-(4"-(4'''-(dimethylamino)phenyl)-1H-1",2",3"-triazol-1"-yl)-2,2'-bipyridine N'-oxide and a second step for preparing 4'-(4"-(4'''-(dimethylamino)phenyl)-1H-1",2",3"-triazol-1"-yl)-2,2'-bipyridine, these steps may be summarized by the following reaction scheme:

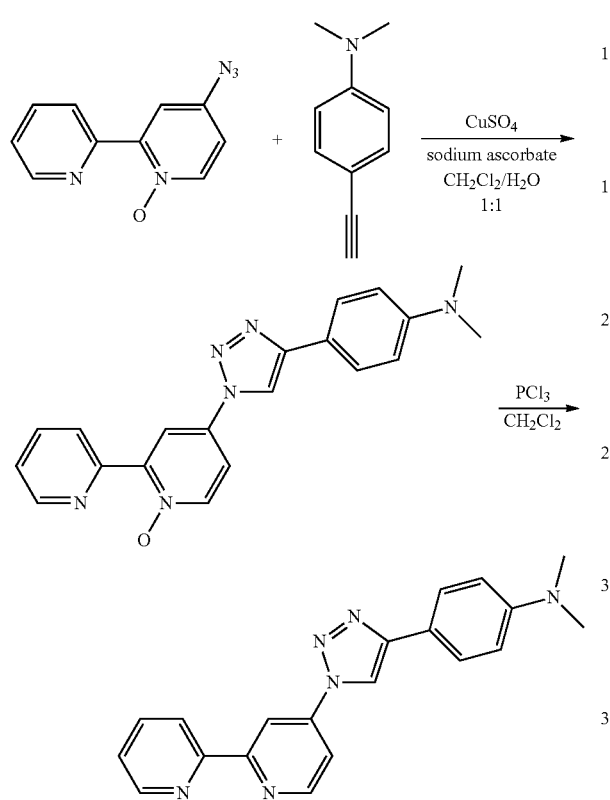

a) Preparation of 4'-(4"-(4'''-(dimethylamino)phenyl)-1H-1",2",3"-triazol-1"-yl)-2,2'-bipyridine N'-oxide Some 4'-azido-2,2'-bipyridine N'-oxide prepared according to Example 1 (32.0 mg, 150 µmol, 1 equiv.) and 4-ethynyl-N,N-dimethylaniline (22.5 mg, 97%, 150 µmol, 1 equiv.) are suspended in methylene chloride (1.20 mL) under an argon atmosphere. Water (1.08 mL) is added to the reaction mixture followed by sodium ascorbate (60 µL, 49.5 mg per mL of water, 15 µmol, 0.1 equiv.) and copper sulfate pentahydrate (60 µL, 31.2 mg per mL of water, 7.5 µmol, 0.05 equiv.) are added sequentially. The reaction mixture is stirred at room temperature for 20 hours. After this period, thin layer chromatography CH$_2$Cl$_2$/methanol (9/1) shows that the coupling reaction is quantitative. The reaction mixture is then diluted with 5 mL of a CH$_2$Cl$_2$/H$_2$O (1/1) mixture and is extracted with methylene chloride (3*5 mL). The organic phases are combined and washed with water, dried with sodium sulfate, filtered and concentrated in order to obtain 51.4 mg (i.e. 96% yield) of an orange solid corresponding to 4'-(4"-(4'''-(dimethylamino)-phenyl)-1H-1",2",3"-triazol-1"-yl)-2,2'-bipyridine N'-oxide of the following formula:

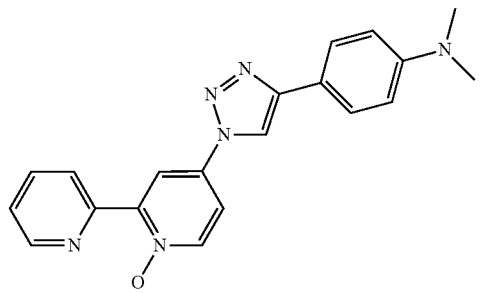

b) Preparation of 4'-(4"-(4'''-(dimethylamino)phenyl)-1H-1",2",3"-triazol-1"-yl)-2,2'-bipyridine To a solution of 4'-(4"-(4'''-(diméthylamino)phenyl)-1H-1",2",3"-triazol-1"-yl)-2,2'-bipyridine N'-oxide prepared beforehand (53.4 mg, 149 µmol, 1 equiv.) in methylene chloride (3.0 mL) under an argon atmosphere, is added phosphorus trichloride (39.0 µL, 61.4 mg, 447 µmol, 3.0 equiv.) at 0° C. The reaction mixture is refluxed for 3 hours, and then poured into 3 mL of ice and neutralized with an aqueous 38.5% sodium hydroxide solution. The aqueous phase is extracted several times with methylene chloride (3*5 mL). The organic phases are then combined and washed with water, and then dried with sodium sulfate, filtered and concentrated. The residue is purified by flash chromatography on silica gel (CH2Cl$_2$/methanol, 95/5), in order to obtain 40.1 mg (i.e. 79% yield) of a yellow powder corresponding to 4'-(4"-(4'''-(dimethylamino)phenyl-1H-1",2",3"-triazol-1"-yl)-2,2'-bipyridine of the following formula:

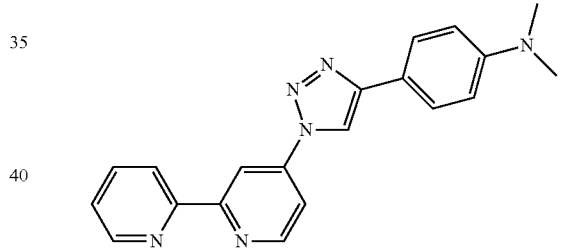

A coordination complex of the following formula:

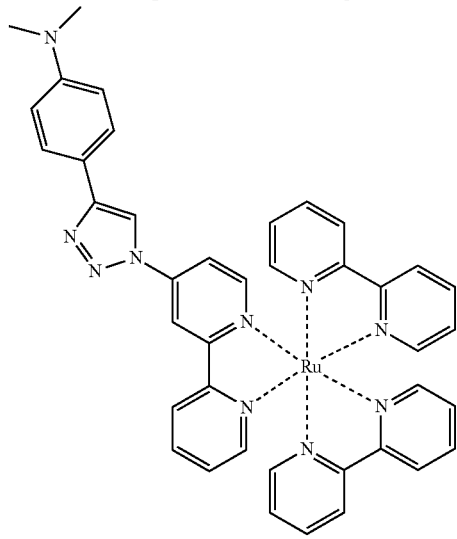

was prepared from the compound synthesized above and from bipyridine compounds.

It was proceeded with measurements of the absorption and emission spectra of this complex, which have a maximum absorption peak at 458 nm and a maximum emission peak at 627 nm (as compared with 451 nm and 608 nm respectively for a ruthenium complex comprising three non-substituted bipyridine groups). It may thus be inferred therefrom that the presence of a triazole group does not perturb the absorption and emission characteristics of the chromophore based on ruthenium.

Tests carried out with this complex in the presence of methylviogen (external electron acceptor) (10 mM of methylviogen in acetonitrile) under an excitation light (energy: 10 mJ; a wavelength λ=450 nm; absorbance A=0.36) gave the possibility of confirming an intramolecular electron transfer from the dimethylamino group towards the chromophore comprising ruthenium (in the $Ru^{3+}$ form). This transfer is very fast (less than 50 ns) as indicated by the kinetics for recovering the $Ru^{2+}$ state. The reduced state of the external electron acceptor is thereby formed very rapidly and proves to be stable for several hundred microseconds.

Thus, it is possible to infer therefrom that the electron transfer from the dimethylamino group towards the chromophore comprising ruthenium via the triazole group is very effective.

As a comparison, similar tests were carried out with a complex of the following formula:

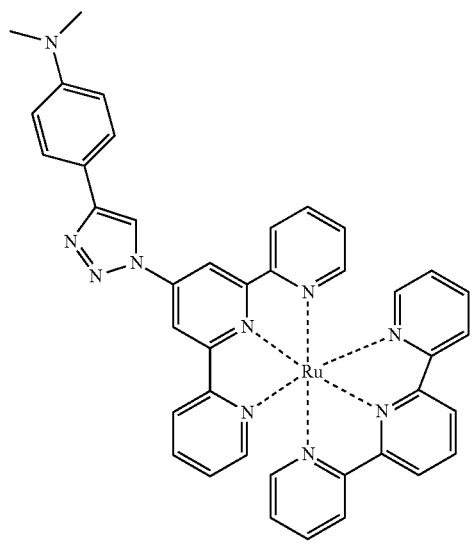

It was ascertained that the intramolecular electron transfer between the dimethylamino group and the chromophore comprising ruthenium through the triazole group is much less effective (a transfer time of more than 20 μs) than for the complex of the invention (transfer time of less than 50 ns).

EXAMPLE 4

This example illustrates the preparation of a compound according to the invention: 4'-(4",(4'''-fluorophenyl)-1H-1", 2",3"-triazol-1"-yl)-2,2'-bipyridine fitting the following formula:

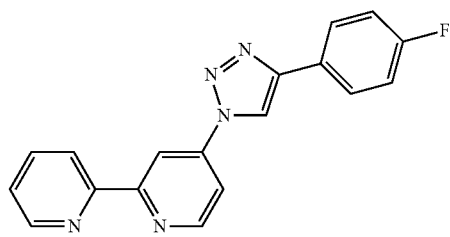 [SMILES: Fc1ccc(-c2cn(-c3ccnc(-c4ccccn4)c3)nn2)cc1]

This compound is prepared in two steps, a first step for preparing: 4'-(4"-(4'''-fluorophenyl)-1H-1",2",3"-triazol-1"-yl)-2,2'-bipyridine N'-oxide and a second step for preparing 4'-(4"-(4'''-fluorophenyl)-1H-1",2",3"-triazol-1"-yl)-2,2'-bipyridine, these steps may be summarized by the following reaction scheme:

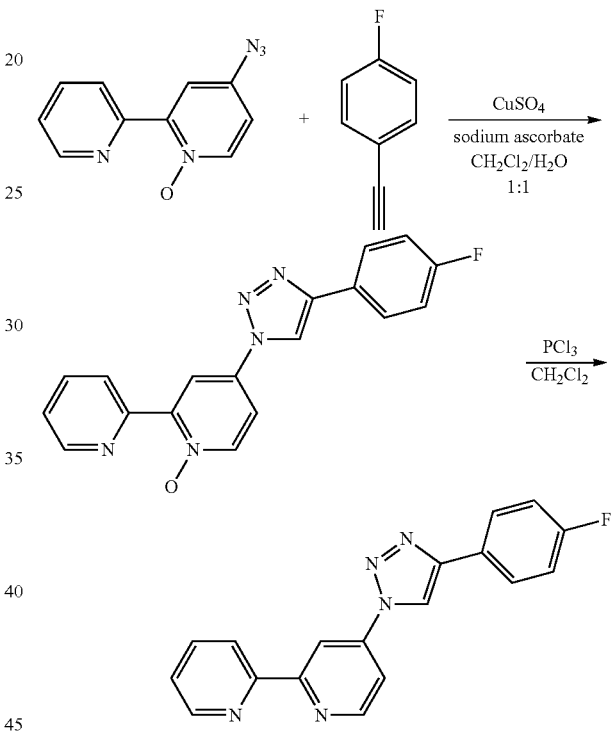

a) Preparation of 4'-(4"-(4'''-fluorophenyl)-1H-1",2", 3"-triazol-1"-yl)-2,2'-bipyridine N'-oxide Some 4'-azido-2,2'-bipyridine N'-oxide prepared according to Example 1 (32.0 mg, 150 μmol, 1 equiv.) is suspended in methylene chloride (1.20 mL) under an argon atmosphere. Some 1-ethynyl-4-fluorobenzene (17.5 μL, 18.4 mg, 98%, 150 μmol, 1 equiv.) is added to the suspension, followed by water (1.08 mL) sodium ascorbate (60 μL, 49.5 mg per mL of water, 15 μmol, 0.1 equiv.) and copper sulfate pentahydrate (60 μL, 31.2 mg per mL of water, 7.5 μmol, 0.05 equiv.) are added sequentially. The reaction mixture is stirred at room temperature for 20 hours. After this period, thin layer chromatography in $CH_2Cl_2$/methanol (9/1) shows that the coupling reaction is quantitative. The reaction mixture is then diluted with 5 mL of a $CH_2Cl_2$/$H_2O$ (1/1) mixture and is extracted with methylene chloride (3*5 mL). The organic phases are combined and washed with water, dried with sodium sulfate, filtered and concentrated in order to obtain 49.2 mg (i.e. 98% yield) of a yellow solid corresponding to 4'-(4''-(4'''-fluorophenyl)-1H-1'',2'',3''-triazol-1''-yl)-2,2'-bipyridine N'-oxide of the following formula:

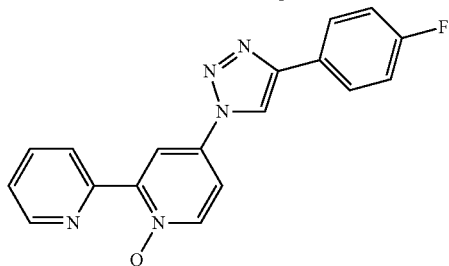

b) Preparation of 4'-(4''-(4'''-fluorophenyl)-1H-1'',2'', 3''-triazol-1''-yl)-2,2'-bipyridine To a solution of 4'-(4''-(4'''-fluorophenyl)-1H-1'',2'',3''-triazol-1''-yl)-2,2'-bipyridine N'-oxide prepared beforehand (47.5 mg, 143 μmol, 1 equiv.) in methylene chloride (2.9 mL), under an argon atmosphere, is added phosphorus trichloride (37.4 μL, 58.9 mg, 429 μmol, 3.0 equiv.) at 0° C. The reaction mixture is refluxed for 3 hours, and then poured into 3 mL of ice and neutralized with an aqueous 38.5% sodium hydroxide solution. The aqueous phase is extracted several times with methylene chloride (3*5 mL). The organic phases are then combined and washed with water, and then dried with sodium sulfate, filtered and concentrated. The residue is purified by flash chromatography on silica gel ($CH_2Cl_2$/methanol, 95/5), in order to obtain 27.2 mg (i.e. 82% yield) of a slightly yellow powder corresponding to 4'-(4''-(4'''-fluorophenyl-1H-1'',2'', 3''-triazol-1''-yl)-2,2'-bipyridine of the following formula:

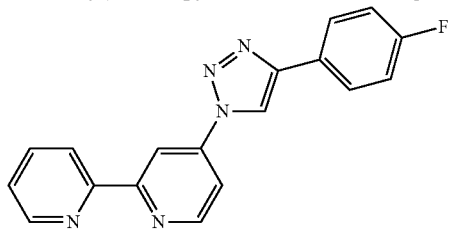 [SMILES: Fc1ccc(-c2cn(-c3ccnc(-c4ccccn4)c3)nn2)cc1]

A coordination complex of the following formula:

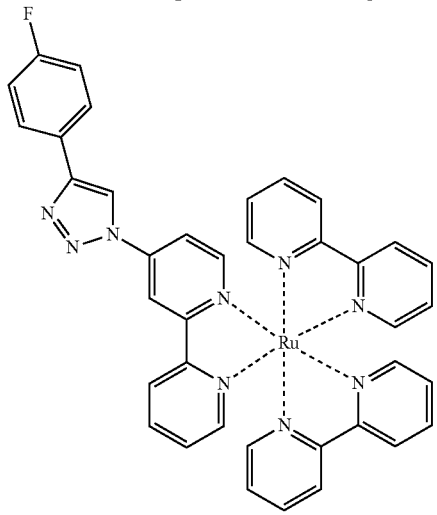

was prepared from the compound synthesized above and from bipyridine compounds.

It was proceeded with measurements of the absorption and emission spectra of this complex, which has a maximum absorption peak at 458 nm and a maximum emission peak at 633 nm (as compared with 451 nm and 608 nm, respectively, for a ruthenium complex comprising three non-substituted bipyridine groups). It is thus possible to infer therefrom that the presence of a triazole group does not perturb the absorption and emission characteristics of the chromophore based on ruthenium.

EXAMPLE 5

This example illustrates the preparation of a compound according to the invention: 4'-(4'',(4'''-(methoxycarbonyl) phenyl)-1H-1'',2'',3''-triazol-1''-yl)-2,2'-bipyridine fitting the following formula:

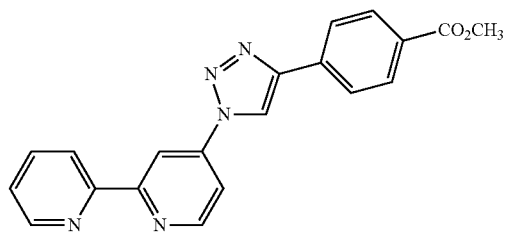 [SMILES: COC(=O)c1ccc(-c2cn(-c3ccnc(-c4ccccn4)c3)nn2)cc1]

This compound is prepared in two steps: a first step for preparing 4'-(4''-(4'''-(methoxycarbonyl)phenyl)-1H-1'',2'', 3''-triazol-1''-yl)-2,2'-bipyridine N'-oxide and a second step for preparing 4'-(4''-(4'''-(methoxycarbonyl)phenyl)-1H-1'', 2'',3''-triazol-1''-yl)-2,2'-bipyridine, these steps may be summarized by the following reaction scheme:

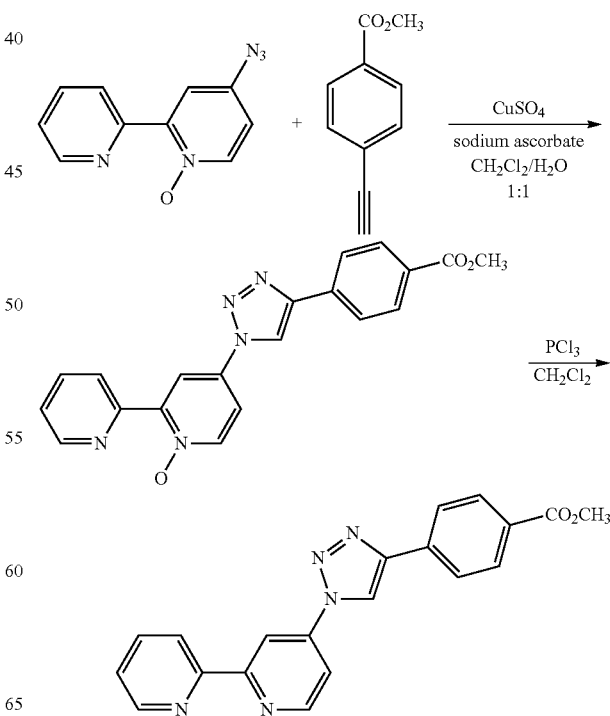

a) Preparation of 4'-(4''-(4'''-(methoxycarbonyl)-phenyl)-1H-1'',2'',3''-triazol-1''-yl)-2,2'-bipyridine N'-oxide Some 4'-azido-2,2'-bipyridine N'-oxide prepared according to Example 1 (32.0 mg, 150 μmol, 1 equiv.) is suspended in methylene chloride (2.50 mL) under an argon atmosphere. Methyl-4-ethynylbenzoate (24.0 mg, 150 μmol, 1 equiv.) is added to the suspension, followed by water (2.38 mL), sodium ascorbate (60 μL, 49.5 mg per mL of water, 15 μmol, 0.1 equiv.) and copper sulfate pentahydrate (60 μL, 31.2 mg per mL of water, 7.5 μmol, 0.05 equiv.) are added sequentially. The reaction mixture is stirred at room temperature for 40 hours. After this period, thin layer chromatography in $CH_2Cl_2$/methanol (9/1) shows that the coupling reaction is quantitative. The reaction mixture is then diluted with 10 mL of a $CH_2Cl_2/H_2O$ (1/1) mixture and is extracted with methylene chloride (3*10 mL). The organic phases are combined and washed with water, dried with sodium sulfate, filtered and concentrated in order to obtain 54.8 mg (i.e. 98% yield) of a yellow solid corresponding to 4'-(4''-(4'''-(methoxycarbonyl)phenyl)-1H-1'',2'',3''-triazol-1''-yl)-2,2'-bipyridine N'-oxide of the following formula:

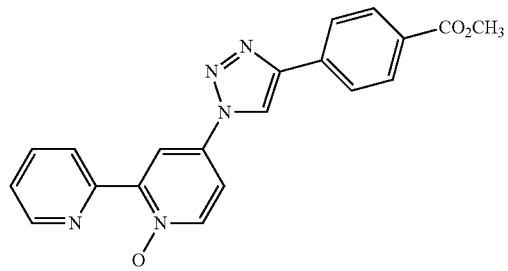

b) Preparation of 4'-(4''-(4'''-(methoxycarbonyl)phenyl)-1H-1'',2'',3''-triazol-1''-yl)-2,2'-bipyridine To a solution of 4'-(4''-(4'''-(methoxycarbonyl)phenyl)-1H-1'',2'',3''-triazol-1''-yl)-2,2'-bipyridine N'-oxide prepared beforehand (54.8 mg, 147 μmol, 1 equiv.) in methylene chloride (6.0 mL) under an argon atmosphere, is added phosphorus trichloride (80.0 μL, 126,0 mg, 916 μmol, 6.2 equiv.) at 0° C. The reaction mixture is refluxed for 3 hours, and then poured into 5 mL of ice and neutralized with an aqueous 38.5% sodium hydroxide solution. The aqueous phase is extracted several times with methylene chloride (3*5 mL). The organic phases are then combined and washed with water, and then dried with sodium sulfate, filtered and concentrated. The residue is purified by flash chromatography on silica gel ($CH_2Cl_2$/methanol, 97/3), in order to obtain 34.0 mg (i.e. 65% yield) of a slightly yellow powder corresponding to 4'-(4''-(4'''-(methoxycarbonyl)phenyl-1H-1'',2'',3''-triazol-1''-yl)-2,2'-bipyridine of the following formula:

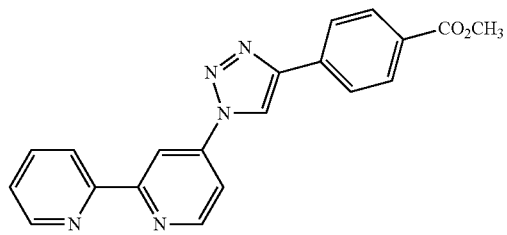 [SMILES: COC(=O)c1ccc(-c2cn(-c3ccnc(-c4ccccn4)c3)nn2)cc1]

A coordination complex of the following formula:

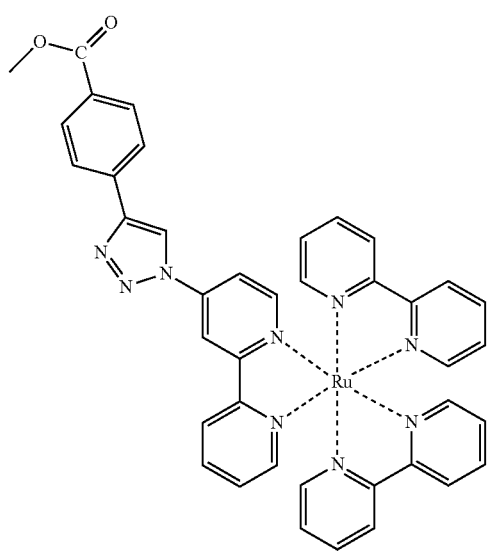

was prepared from the compound synthesized above and from bipyridine compounds.

This complex was then anchored on a titanium dioxide $TiO_2$ substrate via the ester group —$CO_2CH_3$. The emission spectrum of the thereby anchored complex was elaborated and showed a maximum emission peak towards 640 nm.

It may thus be inferred therefrom that the triazole group allows electron transfer from the chromophore comprising ruthenium towards the substrate.

The invention claimed is:
1. A compound of formula (I):

A-T-Z  (I)

wherein:
A is a group capable of complexing at least one metal element, which is a bipyridine group of the following formula:

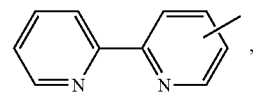

in which the bond located in the middle of the carbon-carbon bond indicates that the binding of the bipyridine group A to the group T of formula (I) is accomplished by any of the carbon atoms of the bipyridine ring;
T is a triazole group directly bound to the group A, said triazole group having the following formula:

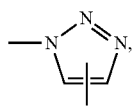

in which the bond located in the middle of the carbon-carbon double bond indicates that the triazole group T is bound to the group A or to the group Z of formula (I) by one of the carbons of the carbon-carbon double bond, while the bond attached to the nitrogen atom of the triazole group T indicates that the triazole group is bound to the other of the group A or the group Z of formula (I) via the nitrogen atom;

Z is a halogen atom, a nitro group, a cyano group, an alkyl group, an aryl group, a heterocyclic group, a group of formula —NR$^1$R$^2$, a group of formula —SR$^1$, a group of formula —S(=O)$_2$(OR$^1$), a group of formula —O—S(=O)$_2$(OR$^1$), a group of formula —O—S(=O)$_2$(R$_1$), a group of formula —S(=O)(OR$^1$), a group of formula —S(=O)(R$^1$), a group of formula —S(=O)$_2$R$^1$, a group of formula —PR$^1$R$^2$, a group of formula —P(=O)(OR$^1$)(OR$^2$), a group of formula —O—P(=O)(OR$^{1)(OR2)}$), a group of formula —O—P(=O)(OR$^1$)(R$^2$), a group of formula —OR$^1$ or a group of formula —CO—R$^1$; and R$^1$ and R$^2$ independently represent a hydrogen atom, an alkyl group or an aryl group, in which said alkyl or aryl groups are optionally substituted.

2. The compound of claim 1, wherein A is a bipyridine group of the formula:

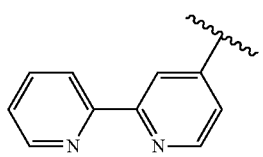

3. The compound of claim 1, wherein Z is an optionally substituted aryl group.

4. The compound of claim 3, wherein:
the aryl group is substituted with at least one halogen atom, at least one group —NR$^1$R$^2$, at least one group —CO$_2$R$^1$, or a combination thereof; and
R$^1$ and R$^2$ independently represent a hydrogen atom, an alkyl group or an aryl group, in which said alkyl or aryl groups are optionally substituted.

5. The compound of claim 1, wherein the compound is of formula (II):

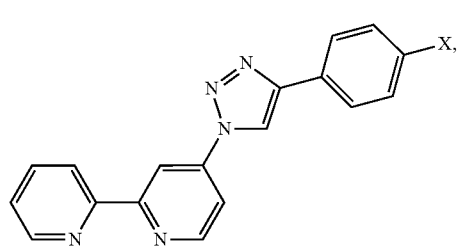

wherein:
X is a hydrogen atom, a halogen atom, a group —NR$^1$R$^2$ or a group —CO$_2$R$^1$; and
R$^1$ and R$^2$ independently represent a hydrogen atom, an alkyl group or an aryl group, in which said alkyl or aryl groups are optionally substituted.

6. The compound of claim 5, wherein X is a hydrogen atom.

7. The compound of claim 5, wherein X is —N(CH$_3$)$_2$.

8. The compound of claim 5, wherein X is —CO$_2$CH$_3$.

9. The compound of claim 5, wherein X is a fluorine atom.

10. A coordination complex of at least one metal element with at least one compound of claim 1.

11. The coordination complex of claim 10, wherein the metal element is at least one selected from the group consisting of a transition metal, a lanthanide element, an actinide element, Al, Ga, Ge, In, Sn, Sb, Tl, Pb, Bi and Po.

12. The coordination complex of claim 10, wherein the metal element is a transition metal.

13. The coordination complex of claim 10, wherein the metal element is ruthenium.

14. The coordination complex of claim 10, further comprising a ligand compound selected from the group consisting of bipyridine and pyridine.

15. A coordination complex of formula (III):

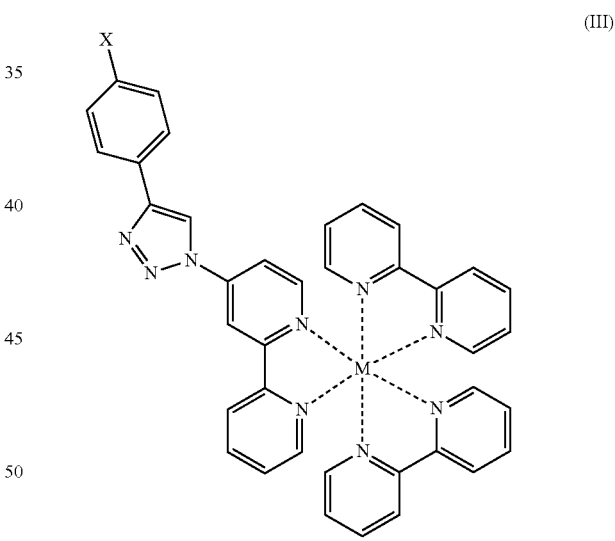

wherein:
X is a hydrogen atom, a halogen atom, a group —NR$^1$R$^2$ or a group —CO$_2$R$^1$;
R$^1$ and R$^2$ independently represent a hydrogen atom, an alkyl group or an aryl group, in which said alkyl or aryl groups are optionally substituted; and
M is a metal element.

* * * * *